(12) United States Patent
Reisinger et al.

(10) Patent No.: US 6,734,319 B2
(45) Date of Patent: May 11, 2004

(54) SEPARATION OF IMPURITIES AND/OR VALUABLE SUBSTANCES FROM SOLUTIONS CONTAINING DIARYL CARBONATE BY SOLUTION CRYSTALLIZATION

(75) Inventors: Claus-Peter Reisinger, Wixom, MI (US); Sven Michael Hansen, Krefeld (DE); Peter Fischer, Köln (DE); Hans-Peter Wirges, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 19 days.

(21) Appl. No.: 10/224,874

(22) Filed: Aug. 21, 2002

(65) Prior Publication Data

US 2003/0109738 A1 Jun. 12, 2003

(30) Foreign Application Priority Data

Aug. 27, 2001 (DE) .......................... 101 41 829

(51) Int. Cl.$^7$ .............................................. C07C 68/06
(52) U.S. Cl. ...................................... 558/274; 502/213
(58) Field of Search ........................... 558/274; 502/213

(56) References Cited

U.S. PATENT DOCUMENTS

| 5,221,798 A | 6/1993 | Mossman | 558/272 |
| 5,239,106 A | 8/1993 | Shafer | 558/274 |
| 5,495,038 A | 2/1996 | Buysch et al. | 687/274 |
| 5,712,406 A | 1/1998 | Buysch et al. | 790/274 |

OTHER PUBLICATIONS

Patent Abstracts of Japan, vol. 2002, No. 02, Apr. 2, 2002 & JP 2001 288148 A (Teijin Ltd), Oct. 16, 2001 Zusammenfassung.
Patent Abstracts of Japan, vol. 2002, No. 02, Apr. 2, 2002 & JP 2001 288149 A (Teijin Ltd), Oct. 16, 2001 Zusammenfassung.

Primary Examiner—Joseph K. McKane
Assistant Examiner—Kamal Saeed
(74) Attorney, Agent, or Firm—Joseph C. Gil; Aron Preis

(57) ABSTRACT

A process for the separation a substantially adduct-free diaryl carbonate from reaction solution is disclosed. The process entails obtaining a solution that contains diaryl carbonate, catalyst system components and an aromatic solvent, lowering the temperature of the solution, optionally in the presence of a nucleating agent, to produce a crystallization product, and washing the crystallization product with an anhydrous wash solution to remove catalyst residues and impurities.

11 Claims, No Drawings

SEPARATION OF IMPURITIES AND/OR VALUABLE SUBSTANCES FROM SOLUTIONS CONTAINING DIARYL CARBONATE BY SOLUTION CRYSTALLIZATION

FIELD OF THE INVENTION

The present invention relates to a process and more particularly to a process for separating off impurities from reaction solutions.

SUMMARY OF THE INVENTION

A process for the separation a substantially adduct-free diaryl carbonate from reaction solution is disclosed. The process entails obtaining a solution that contains diaryl carbonate, catalyst system components and an aromatic solvent, lowering the temperature of the solution, optionally in the presence of a nucleating agent, to produce a crystallization product, and washing the crystallization product with an anhydrous wash solution to remove catalyst residues and impurities.

BACKGROUND OF THE INVENTION

U.S. Pat. No. 5,239,106 disclosed the separation of diphenyl carbonate (DPC) from catalyst-containing reaction solutions by crystallization of the 1:1 adduct of DPC with phenol, comprising 30.5 wt. % phenol and 69.5 wt. % diphenyl carbonate, with the aid of suspension crystallization. A disadvantage of this process that it is limited to a narrow concentration range in order to be able to isolate the 1:1 adduct in a sufficiently high yield, i.e. diphenyl carbonate concentrations of at least 50 wt. % to 70 wt. % in the reaction solution.

In order still to be able to process the resulting suspensions by filtration techniques, at least a two-stage procedure requiring expensive equipment is necessary.

Furthermore, the catalyst system in this process may not be separated off completely, since the crystals filtered off are still contaminated by adhering mother liquor and inclusions of mother liquor. During subsequent working up of the 1:1 adduct by distillation, these catalyst constituents which have not been separated off have an adverse effect due to catalysis of by-product formation and DPC decomposition. The proposed washing of the crystallization product with a mixture of 9% water and 91% phenol (see column 3, lines 14–18) reduces the yield by the dissolving of large portions of the 1:1 adduct.

This treatment moreover leads to an increase in the water content of the adduct crystals, resulting in DPC losses by hydrolysis in the subsequent distillation columns, i.e. for DPC isolation and for separating water off from the wash solution used. Furthermore, essential process parameters, e.g. relating to the nature of the reactor, the temperature program, stirrer geometry, stirrer output etc., are not disclosed in U.S. Pat. No. 5,239,106.

In order to process reaction solutions where the DPC content is less than 50 wt. % by this process, concentration by distillation is essential, with the disadvantages described above of distillation in the presence of catalyst constituents. In addition, exposure of the reaction solution to heat leads to a deactivation of the catalyst system, which requires an expensive fresh feed of the catalyst components into the process. All these disadvantages described make the process inflexible and unattractive and obstruct industrial realization.

EP-A 0 687 666 described a process for the purification of diphenyl carbonate by fractional melt crystallization of highly concentrated reaction solutions in the temperature range of 45–85° C. The diphenyl carbonate purities which may be achieved are between 97.5 and 99.5%. A disadvantage of this process is the limitation to reaction solutions with a diaryl carbonate content of greater than 70 wt. %. Reaction solutions with diaryl carbonate contents below 70 wt. % may not be processed by this process and would therefore have to be concentrated to the required contents, for example by distillation. During this exposure to heat, the catalyst system causes side reactions and is thereby deactivated itself. For these reasons the process is uneconomical and cumbersome for reaction solutions with diphenyl carbonate contents below 70 wt. %.

There is therefore interest in discovering a gentle method which allows catalyst components to be recovered in a high yield and to be recycled into the reaction without significant deactivation of the catalyst system and under economical conditions which may be realized and reproduced industrially, from solutions which comprise the hydroxyaromatic compound employed and diaryl carbonate in various compositions.

DETAILED DESCRIPTION OF THE INVENTION

It has now been found, surprisingly, that the disadvantages described may be overcome if the reaction mixture is crystallized in an aromatic solvent. In a completely surprising manner, substantially adduct-free diaryl carbonate may be obtained by this procedure even at diaryl carbonate concentrations below 70 wt. %. The crystallization may be carried out very efficiently at moderate crystallization start and end temperatures. Thermal damage of the catalyst system therefore does not take place by this process, which reduces deactivation of the catalyst to a minimum. By the combination of a crystallization and a washing of the crystals, the catalyst constituents may surprisingly be separated off almost completely. The mother liquor comprising catalyst constituents may then be recycled again into the reactor or worked up. The invention accordingly relates to a method for separating off the catalyst system and substantially adduct-free diaryl carbonate, wherein the catalyst systems may include a platinum metal catalyst, a cocatalyst, a bromide salt and a base, from reaction solutions which comprise aromatic carbonates of the formula (I)

R—O—CO—O—R (I)

in which R denotes a substituted or unsubstituted $C_6$–$C_{24}$-aryl, and at least one aromatic hydroxy compound of the formula (II)

R—O—H (II)

wherein R has the above mentioned meaning, comprising
    a) obtaining a solution that contains hydroxy an aromatic compound, diaryl carbonate and catalyst system in an aromatic solvent,
    b) lowering the temperature of the solution, optionally introducing seeding materials, to bring about crystallization to produce a crystallization product and mother liquor that contains the catalyst system,
    c) separating the catalyst-containing mother liquor from the crystallization product, and optionally
    d) recycling the mother liquor for the preparation of a diaryl carbonate or working up the mother liquor, and (optionally)

e) washing the crystallization product to remove the catalyst system.

Embodiments which utilize the parameters, compounds, definitions and explanations mentioned as preferred, particularly preferred or very particularly preferred are preferred, particularly preferred or very particularly preferred.

However, the definitions, parameters, compounds and explanations mentioned above generally or mentioned in preferred ranges may also be combined as desired with one another, that is to say between the particular ranges and preferred ranges.

The catalyst system includes at least one noble metal of group VIIIB, preferably palladium. It may be added in various forms in the process according to the invention. Palladium may be employed in metallic form, e.g. as palladium black or on a support, such as Pd/C, Pd/Al$_2$O$_3$ or Pd/SiO$_2$, or preferably in the form of palladium compounds of oxidation levels 0 and +2, such as, for example, palladium (II) acetylacetonate, halides, carboxylates of C$_2$–C$_{18}$-carboxylic acids, dicarboxylates, such as oxalate, nitrate, sulfate or oxides, or palladium complexes which may comprise, for example, carbon monoxide, olefins, amines, nitriles, phosphorus compounds and halides. Palladium bromide and palladium acetylacetonate are particularly preferred.

The amount of catalyst present is not limited in the process according to the invention. Preferably, catalyst is added in an amount such that the concentration of the metal in the reaction mixture is 1 to 3,000 ppm, and concentrations of 5 to 500 ppm are particularly preferred.

A metal of groups III A, III B, IV A, IV B, V B, I B, II B, VI B or VII B, of the rare earth metals (atomic numbers 58–71) or of the iron group of the periodic table of the elements (Mendeleev), optionally also mixtures thereof, is present as a metal salt acting as a cocatalyst for the process according to the invention, it being possible for the metal to be employed in various oxidation levels. (See e.g. U.S. Pat. Nos. 5,142,086, 5,231,210, and 5,284,964, EP-A 350 697, EP-A 350 700, and U.S. Pat. No. 5,336,803) Pb, Ti, Mn, Cu, Co, V, Zn, Ce and Mo are preferably employed. Without limiting the process according to the invention, lead(II), manganese(II), manganese(III), copper(I), copper(II), cobalt (II), cobalt(III), vanadium(III) and vanadium(IV), in particular manganese(II), manganese(III), cobalt(II) and cobalt (III), may be mentioned. The metals may be employed, for example, as halides, oxides, carboxylates of C$_2$–C$_{18}$-carboxylic acids, diketonates or nitrates and as complex compounds which may comprise, for example, carbon monoxide, olefins, aromatic and aliphatic mono- or polyamines, phosphorus compounds, pyridines, bipyridines, terpyridines, quinolines, isoquinolines, cryptands, Schiff's bases and halides. Mn, Cu, Mo, Pb and Ce are particularly preferably employed. Manganese compounds are very particularly preferably used in the process according to the invention, particularly preferably complexes of manganese (II) and manganese(III), very particularly preferably manganese(II) acetylacetonate or manganese(III) acetylacetonate, and manganese(II) bromide.

The cocatalyst is present in a concentration in the range from 0.0001 to 20 wt. % of the reaction mixture, and the concentration range of 0.001 to 5 wt. % is preferred, particularly preferably 0.005 to 2 wt. %.

The bromide compounds mentioned in the context of the present invention are, for example, the alkali metal bromides or alkaline earth metal bromides, but preferably the bromide salts of organic cations. The organic cations may be, for example, ammonium, guanidinium, phosphonium or sulfonium salts substituted by organic radicals, and optionally also mixtures thereof. Ammonium, guanidinium, phosphonium and sulfonium salts which contain C$_6$- to C$_{10}$-aryl, C$_7$- to C$_{12}$-aralkyl and/or C$_1$- to C$_{20}$-alkyl radicals as organic radicals are suitable for use in the process according to the invention. Ammonium salts which carry C$_6$- to C$_{10}$-aryl, C$_7$- to C$_{12}$-aralkyl and/or C$_1$- to C$_{20}$-alkyl radicals as organic radicals are preferably present, and tetrabutylammonium bromide and tetrabutylphosphonium bromide are particularly preferred. The amount of the bromide compound is 0.1–20 wt. %, based on the weight of the reaction mixture. This amount is preferably 0.5–15 wt. %, particularly preferably 1–5 wt. %.

Bases which are present in the process according to the invention are alkali metal hydroxides, alkali metal salts or quaternary salts of weak acids, such as alkali metal tert-butylates, or alkali metal salts or quaternary salts of aromatic hydroxy compounds of the formula, (II), in which R has the abovementioned meaning. An alkali metal salt or quaternary salt of the aromatic hydroxy compound of the formula (II) which has also been reacted to give the organic carbonate, for example tetrabutylammonium or potassium phenolate, is very particularly preferably present.

Salts of lithium, sodium, potassium, rubidium or caesium may be present as alkali metal salts. Lithium, sodium and potassium phenolates are preferably present, particularly preferably potassium phenolate.

Ammonium, phosphonium, pyridinium, sulfonium or guanidinium salts which have C$_6$- to C$_{18}$-aryl, C$_7$- to C$_{18}$-aralkyl and/or C$_1$- to C$_{20}$-alkyl radicals as organic radicals may be present as quaternary salts. The radicals may all be identical or different, and mixtures of several quaternary salts may optionally also be employed. The same cation which is also present as the bromide is optionally preferably present here. Tetraphenylphosphonium, tetrabutylammonium and tetrabutyl-phosphonium are furthermore preferred, and tetrabutylammonium is particularly preferred.

Alternatively, trialkylamine bases, such as tributylamine, diisopropylethylamine, DBU or DBN, may also be present.

The base is present in an amount independent of the stoichiometry. The ratio of platinum metal, e.g. palladium, to base is preferably such that 0.1 to 5,000, preferably 1 to 1,000, particularly preferably 10 to 300 equivalents of base are present per mol of platinum metal, e.g. palladium.

According to the invention, the aromatic hydroxy compounds R—O—H are preferably optionally substituted monohydroxy compounds, such as phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphnol, 1-naphthol and 2-naphthol, and phenol and o-, m- and p-cresol are particularly preferred, very particularly preferably phenol.

In the case of substitution of the aromatic hydroxy compounds, this is generally by 1 to 6 substituents such as C$_1$–C$_{18}$-alkyl, C$_6$–C$_{24}$-aryl, C$_7$–C$_{24}$-aralkyl, C$_1$–C$_{18}$-alkoxy, fluorine, chlorine or bromine.

Di- or polyhydroxy compounds, such as resorcinol and hydroquinone, and tris- and bisphenols, such as 2,2-bis-(4-hydroxyphenyl)-propane (bisphenol A), 2,2-bis-(3,5-dimethyl-4-hydroxyphenyl)-propane, 1,1-bis-(4-hydroxyphenyl)-cyclohexane, 1,1-bis-(4-hydroxyphenyl)-3,3,5-trimethylcyclohexane or 6,6'-dihydroxy-3,3,3',3'-tetramethyl-1,1'-spiro(bis)-indane, 2,4'-hydroxybiphenyl or 4,4'-hydroxybiphenyl, may be reacted in a similar manner to give oligo-aryl carbonates. Such solutions comprising oligocarbonates and catalyst components may also be worked up according to the process according to the invention. Mixtures of oligocarbonates with diaryl carbonates and optionally catalysts may furthermore also be worked up in a corresponding manner and subsequently reacted further in solid phase or melt reactions.

Unsubstituted or mono- to hexasubstituted mono- or polynuclear aromatic compounds may be employed as the aromatic solvent. Suitable substituents include $C_1$–$C_{20}$-alkyl, $C_7$–$C_{20}$-aralkyl, $C_6$–$C_{30}$-aryl or alkoxy radicals, nitro groups, sulfonates, sulfones or halogens. Examples include benzene, toluene, anisole, chlorobenzene, dichlorobenzenes, fluorobenzene, xylenes, mesitylene, naphthalene and biphenyl. The aromatic solvent preferably has a boiling point of about 70 to 180° C., particularly preferably about 80 to 150° C. Mixtures of aromatic solvents may also be employed, but pure solvents are preferred. Chlorobenzene or chlorobenzene-containing solvent mixtures are particularly preferably employed, very particularly preferably chlorobenzene.

The solvent in step a) is used in a concentration of about 3 to 80 wt. %, preferably 10 to 60 wt. %, particularly preferably 20 to 50 wt. %, based on the weight of the total reaction mixture. The desired concentration may be adjusted, depending on the previous history of the reaction mixture, by dilution with solvent or conversely by concentration steps known to the expert for partial separating off of the solvent, e.g. by vacuum distillation. A portion of the hydroxyaromatic compound ROH may optionally also be separated off at the same time here.

The dilution of the reaction mixture in step a) may be omitted if the reaction is already carried out in an aromatic solvent. The solvent of the reaction is then preferably also employed for the crystallization, since separation and mixing operations may thus be avoided.

Crystallization technologies such as are described in detail, for example, in Chem.-Ing.-Techn. 57 (1985) 91 et seq. or J. W. Mullin in Ullmann's Encyclopedia of Industrial Chemistry, 6th ed., 2001 electronic release: Crystallization and Precipitation, may be employed in step b) for the process according to the invention. The stirred tank crystallizers often used (cf. Chem.-Ing.-Techn. 57 (1985) p. 95) may have dimensions according to the specifications and recommendations of M. Zlokarnik, H. Judat in Ullmann's Encyclopedia of Industrial Chemistry, 6th ed., 2001 electronic release: Stirring. These processes are carried out discontinuously or continuously. All the apparatuses have heat exchange surfaces and a cooling circulation; the temperatures stated below are those of the coolant recycling from the heat exchange surfaces.

For example, the solution crystallization may be carried out in a discontinuous stirred crystallizer with an anchor-type stirrer or cross-bar stirrer without baffles.

A specific stirrer output (P/V) of about 0.02 to 5 W/l may be used during the crystallization. Specific stirrer outputs of about 0.05 to 2 W/l are preferably used, particularly preferably about 0.2 to 0.5 W/l.

The cooling in step b) may be carried out according to various temperature/time profiles. Linear profiles with a constant rate of cooling and convex profiles in which the rates of cooling at the start of the crystallization are lower than towards the end of the crystallization are preferred.

The variable or fixed cooling rates are in the range of 0.01 to 20 K/h. The cooling rate is preferably always less than about 10 K/h, and is particularly preferably in the range from about 0.5 to 8 K/h, very particularly preferably in the range from about 1 to about 6 K/h.

The starting temperature for the cooling depends on the starting concentration of diaryl carbonate, and the cooling end temperature depends on the desired suspension concentration. The cooling end temperature is preferably adjusted here such that a solids content of about 10 to 40 wt. %, particularly preferably about 15–30 wt. %, is present at this temperature.

A start temperature of about 20 to 60° C., preferably about 25 to 40° C., particularly preferably about 28 to 38° C., is used in the particularly preferred process of the invention. The desired suspension concentration may be achieved by cooling by a surprisingly small temperature difference of about 20 to 40 K to end temperatures of about −10 to 20° C., preferably about 0 to 15° C. Both the crystallization start and the end temperature are thus in a range which is very favorable for an industrial procedure.

The system is preferably seeded with a nucleating agent at the crystallization start temperature, and the diaryl carbonate which is to be crystallized is particularly preferably employed here. The amount of nucleating agent is about 0.01 to 10%, preferably about 0.02 to 1%, based on the yield of solid obtained after the crystallization.

An post-stirring period of about 1 to 2 hours is preferably maintained at the cooling end temperature.

In step c), the catalyst-containing mother liquor formed is separated from the crystallization product by known processes, such as e.g. decanting off, pressing off, filtering off with suction, filtration, centrifugation etc.

The mother liquor obtained is optionally combined in step d) with further solutions obtained during washing and may be passed back into the reaction, for recycling of the catalyst components, directly or after further working up steps, e.g. complete or partial separating off of the solvent. Alternatively, some or all of the mother liquor may be worked up to obtain the valuable substances, e.g. platinum group metals. Recycling is the preferred variant.

The crystallization product formed surprisingly comprises not an adduct (e.g. phenol-diphenyl carbonate adduct) but substantially diphenyl carbonate even at low diaryl carbonate contents.

Impurities, such as catalyst components, by-products or, where appropriate, also hydroxyaromatic ROH, may be separated off further in a preferred working up variant e) by washing the crystallization product with an anhydrous wash solution, e.g. by suspending the crystallization product.

Suitable wash solutions have the lowest possible (additional) solubility for diaryl carbonates, but a good solubility for the components otherwise still present in the reaction mixture.

Substances intrinsic to the system are preferably used as the wash solution, e.g. the hydroxyaromatic ROH, the diaryl carbonate, the solvent or mixtures of these compounds. Washing is particularly preferably carried out with the substantially pure crystallization solvent. A mixture which substantially comprises solvent/diaryl carbonate or solvent/diaryl carbonate/ROH is very particularly preferably used for the washing, solutions which are saturated with diaryl carbonate and contain as little ROH as possible preferably being used here.

In the particularly preferred process of crystallization of diphenyl carbonate from mixtures of phenol in the solvent chlorobenzene, washing is thus preferably carried out with chlorobenzene or chlorobenzene/diphenyl carbonate solutions or chlorobenzene/diphenyl carbonate/phenol solutions.

The washing solution is preferably maintained at a temperature of about −15 to 50° C., particularly preferably about −10 to 20° C., where washing solution which are not saturated with diary carbonate should be as cold as possible. Washing is very particularly preferably carried out at about the crystallization end temperature with a saturated solution of the diaryl carbonate.

The washing step is carried out with an amount of about 20 to 500 wt. %, preferably about 40 to 400, particularly preferably about 50 to 350 wt. %, of the washing solution, based on the filter cake.

In a preferred manner, the crystallization product is treated with portions of the washing solution in several operations, for example such that the crystallization product is first suspended in 25 to 40 wt. % of the total amount of the wash liquid and filtered and the operation is then repeated with a further 60 to 75 wt. %.

The washing solution may include, where appropriate, catalyst components, hydroxyaromatic compound ROH and, where appropriate, by-products. It may be worked up in various ways to obtain or separate off these components. Variants in which all or some of the washing solution is recycled into the reaction are preferred. Preferably, the washing solution, optionally after working up, e.g. partial or complete separating off of the solvent, is combined with the mother liquor, optionally worked up further and/or recycled into the reaction.

The crystallization product is further purified during the washing and surprisingly includes substantially adduct-free diaryl carbonate with adhering solvent residues. For further working up, the diaryl carbonate may be freed from adhering solvent e.g. by applying a vacuum or washing with a further, more readily volatile wash liquid. The further washing solution may then also be separated off by applying a vacuum. A purity which is required for the intended use may optionally already be achieved here.

Further possible working up variants are e.g. extraction, further solution crystallizations or melting and subsequent distillation, or fractional melt crystallizations, and other known purification processes.

The invention also provides the separation of diaryl carbonate R—O—CO—O—R from mixtures which comprise hydroxyaromatics ROH and optionally further impurities, in addition to the diaryl carbonate.

The crystallization product obtained in fact surprisingly contains no adducts of ROH and R—O—CO—O—R, even in the case of mixtures with far less than 70 wt. % phenol, but, as already mentioned, on the contrary substantially includes pure diaryl carbonate and solvent. It thus offers a purification process for diaryl carbonates which is efficient and not particularly energy-intensive compared with distillation.

A particular advantage of the process according to the invention is that reaction solutions in which the diaryl carbonate content is present in a an amount ranging from about 25 to 95 wt. % may be used. Mixtures of various diaryl carbonates, e.g. cresyl phenyl carbonate and diphenyl carbonate, may also be contained in the reaction solutions which may be employed, and may be purified by the process according to the invention.

The processes according to the invention are preferably employed in the oxidative direct carbonylation of ROH to diaryl carbonates R—O—CO—OR, but are in no way limited only to this. The process may also be very readily used e.g. in the preparation of diaryl carbonates by transesterification of dialkyl carbonates or other diaryl carbonates or in the decarbonylation of diaryl oxalates. In principle, it may also be employed in preparation processes based on the reaction of ROH with phosgene.

However, the process according to the invention may also be employed for purification of contaminated diaryl carbonate (DAC) containing mixtures formed elsewhere, in which A a solution of the mixture in an aromatic solvent is prepared, B a solution crystallization is initiated by lowering the temperature and optionally seeding, C the mother liquor is separated off from the crystallization product, and optionally D the substantially adduct-free crystallization product is washed with a washing agent.

The progress and the suitable solvents/parameters here are the same as described above for working up a reaction solution.

The following examples are intended to illustrate the subject matter of the present Application, but without limiting it.

In the examples, tetrabutylammonium bromide (TBAB) is regarded as an example of an impurity or catalyst component to be recycled. TBAB represents a substance which occurs as the catalyst component with the highest concentration in the feed and the purification factor of which in the crystallization product may be measured the most easily. The reaction solutions may be obtained e.g. by known processes for the preparation of diaryl carbonates, e.g. in accordance with DE-A 19 605 167.

The examples are based on the particularly preferred preparation of diphenyl carbonate from phenol; however, it is easy for the expert to adapt the conditions to be established to the physical data of other diaryl carbonates.

EXAMPLES

Reaction solutions which comprised, inter alia, phenol, diphenyl carbonate (DPC), monochlorobenzene (MCB) and tetrabutylammonium bromide (TBAB) were added as a feed into a stirred crystallizer; by use of several crystallizers in cycles a quasi-continuous procedure may be realized. The crystallization conditions are stated in each case. The composition of the starting reaction mixture, crystallization product and mother liquor is analysed by gas chromatography, it being possible for the weights of the components to be determined by means of an internal standard. The TBAB content is calculated from its thermal decomposition product tributylamine.

Example 1

A reaction mixture from the aromatic direct carbonylation of phenol with a composition of 35.6 wt. % MCB, 17.0% phenol, 7.2% tetrabutylammonium bromide and 40.2% diphenyl carbonate is crystallized in a stirred crystallizer with a cross-bar stirrer under a specific stirrer output P/V= 0.2 W/l. The mixture is seeded with diphenyl carbonate at 34° C. and cooled at a cooling rate of 5 K/h and the solids content of the reaction mixture is determined. The result is shown in Table 1.

TABLE 1

| Temperature [° C.] | 34 | 32 | 30 | 27.5 | 24 | 20 | 10 |
|---|---|---|---|---|---|---|---|
| Solids content [wt. %] | 0 | 6 | 8 | 11 | 14 | 17 | 23 |

Example 2

500 g of a mixture containing 35.1 wt. % MCB, 16.2% phenol, 8.1% tetrabutylammonium bromide and 40.6% diphenyl carbonate is seeded with 0.1 g DPC at 31° C. and cooled with a stirred crystallization apparatus with a cooling rate of 5 K/h to a final temperature of 25° C. The crystals are filtered off and then washed with 100 ml of a saturated solution of DPC in MCB. 109.1 g of crystals are obtained. The compositions of the mother liquor, unwashed crystals and washed crystals are shown in Tab. 2.

TABLE 2

|  | MCB | Phenol | TBAB | DPC |
|---|---|---|---|---|
| Mother liquor [wt. %] | 40.6 | 19.9 | 9.5 | 30.9 |
| Unwashed crystals [wt. %] | 15.7 | 10.9 | 5.2 | 69.2 |
| Washed crystals [wt. %] | 24.5 | 0.5 | 0.0 | 74.8 |

Example 3

900 g of a mixture containing 35.1 wt. % MCB, 16.2% phenol, 8.1% tetrabutylammonium bromide and 40.6% diphenyl carbonate is seeded with 1% diphenyl carbonate at 34° C. and then cooled with a cooling rate of 5 K/h to a crystallization end temperature of 10° C. The crystals are filtered off and then washed with various amounts of a saturated solution of diphenyl carbonate in chlorobenzene and after-washed with 10 ml cyclohexane. The results, expressed as the amount of washing agent relative to the weight of the filter cake, are shown in Tab. 3.

TABLE 3

| Amount of washing agent [wt. %] | 0 | 50 | 150 | 250 |
|---|---|---|---|---|
| TBAB [wt. %] | 6.1 | 1.2 | 0.7 | <0.2 |

Example 4

A reaction mixture of 900 g obtained from the aromatic direct carbonylation of phenol with a composition of 35.6 wt. % MCB, 17.0% phenol, 7.2% tetrabutylammonium bromide and 40.2% diphenyl carbonate is crystallized in a stirred crystallizer with an anchor-type stirrer under a specific stirrer output P/V=0.2 W/l. The mixture is seeded with diphenyl carbonate at 34° C., cooled with various linear cooling rates to a final temperature of 20° C. and filtered and the filter cake is washed with a DPC-saturated MCB solution (volume ratio of wash liquid/filter cake=2/1) and then washed with 50 ml n-hexane. The TBAB content of the crystallization product is determined. The result is shown in Tab. 4.

TABLE 4

| Cooling rate [K/h] | 10 | 5 | 2 |
|---|---|---|---|
| TBAB [wt. %] | 3.0 | 0.6 | <0.2 |

Example 5

A mixture containing 35.1 wt. % MCB, 16.2% phenol, 8.1% tetrabutylammonium bromide and 40.6% diphenyl carbonate is seeded with 1% diphenyl carbonate at 34° C. in a stirred crystallizer with an anchor-type stirrer under various specific stirrer outputs and then cooled with a cooling rate of 5 K/h to a crystallization end temperature of 20° C. The crystals are filtered off and then washed with a DPC-saturated MCB solution (volume ratio of wash liquid/filter cake=2/1). The TBAB content of the crystallization product is shown in tab. 5. The average particle size at all the stirrer outputs is between about 100 and 150 micrometres.

TABLE 5

| Specif. stirrer output P/V [W/l] | 0.05 | 0.1 | 0.2 | 0.4 |
|---|---|---|---|---|
| TBAB [wt. %] | 1.6 | 1.1 | <0.2 | <0.2 |

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A Process for separating off catalyst system components from a reaction mixture which contains diaryl carbonate and aromatic hydroxy compounds, comprising
    a) obtaining a solution containing an aromatic hydroxy compound, diaryl carbonate, catalyst system components and an aromatic solvent,
    b) lowering the temperature of said solution, optionally in the presence of a nucleating agent to produce a crystallization product and mother liquor,
    c) separating off the mother liquor that contains the catalyst system from the crystallization product, and optionally
    d) recycling or working up the mother liquor, and optionally
    e) washing the crystallization product with an anhydrous wash solution to remove adhering catalyst residues and impurities wherein catalyst system components comprise at least one member selected from the group consisting of platinum metal catalyst, cocatalyst, bromide salt and a base.

2. The process according to claim 1 in which the diaryl carbonate is diphenyl carbonate and the aromatic hydroxy compound is phenol.

3. The process according to claim 1 wherein aromatic solvent contains chlorobenzene.

4. The process according to claim 1 wherein in which the content of the solvent is about 3 to 80% relative to the weight of the reaction mixture.

5. The process according to claim 1 wherein lowering of the temperature of said solution is in the presence of a nucleating agent.

6. The process of claim 5 wherein the amount of said nucleating agent is 0.01 to 10% relative to the weight of the crystallization product.

7. The process according to claim 5 where the nucleating agent contains crystals of the crystallization product.

8. The process of according to claim 1 wherein solution in step b) is at 20 to 60° C. and where said solution is cooled at a rate of 0.01 to 20 K/h to a final temperature of about −10 to 20° C.

9. The process according to claim 1 in which washing is carried out with a washing solution selected from the group consisting of solvent, mixture of solvent/diaryl carbonate and mixture of solvent/diaryl carbonate/hydroxyaromatic.

10. The process according to claim 1 in which the amount of washing solution is 20 to 500% relative to the weight of the crystallization product.

11. The process according to claim 1 in which step b) is carries out in an apparatus having specific stirrer output of about 0.02 to 5 W/l.

* * * * *